United States Patent [19]

Middleditch et al.

[11] Patent Number: 5,369,031
[45] Date of Patent: Nov. 29, 1994

[54] BIOREMEDIATION OF POLAR ORGANIC COMPOUNDS

[75] Inventors: Brian S. Middleditch; Peter S. K. Lee, both of Houston, Tex.
[73] Assignee: University of Houston, Houston, Tex.
[21] Appl. No.: 918,713
[22] Filed: Jul. 21, 1992
[51] Int. Cl.$^5$ ............................ C12F 1/04; C02F 3/30; C02F 3/34
[52] U.S. Cl. ................................... 435/284; 435/170; 435/262; 435/262.5; 435/264; 435/281
[58] Field of Search ..................... 435/41, 262.5, 262, 435/264, 281, 170, 832

[56] References Cited

U.S. PATENT DOCUMENTS

| | | | |
|---|---|---|---|
| 4,871,673 | 10/1989 | Rehm et al. | 435/264 |
| 4,992,174 | 2/1991 | Caplan et al. | 435/281 |
| 5,178,491 | 1/1993 | Graves et al. | 435/262 |
| 5,186,842 | 2/1993 | Jolly | 435/264 |
| 5,209,851 | 5/1993 | Hume et al. | 435/262 |

FOREIGN PATENT DOCUMENTS

| | | | |
|---|---|---|---|
| 0044685 | 4/1976 | Japan | 435/262 |
| 1620479 | 1/1991 | U.S.S.R. | 435/262 |

OTHER PUBLICATIONS

E. M. Bonnet-Smits, et al., "Carbon dioxide fixation as the initial step in the metabolism of acetone by Thiosphaera pantotropha" *J. Genl. Microbiol*, 134:2281-2289 (1988).
J. P. Coleman, et al., "Fate of the $C_1$ product of propane dissimilation in *Mycobacterium vaccae*" *J. Bacteriol.* 160:1163-1164 (1984).
M. J. DiGeronimo, et al., "Metabolism of acetonitrile and propionitrile" *Appl. Environ. Microbiol.* 31:900-906 (1976).
G. Fuchs, et al., "Autotrophic $CO_2$ fixation in *Chlorobium limicola*. Evidence for the operation of a reductive tricarboxylic acid cycle in growing cells" Arch. Microbiol. 128:64-71 (1980).
B. R. Landau, et al., "The role of acetone in the conversion of fat to carbohydrate" *TIBS* (12):113-114 (1987).
H. B. Lukins, et al., "Methyl ketone metabolism in hydrocarbon-utilizing mycobacteria" *J. Bacteriol.* 85:1074-1087 (1963).
H. Platen, et al., "Methanogenic degradation of acetone by an enrichment culture" *Arch. Microbiol.* 149:136-141 (1987).
H. Platen, et al., "Anaerobic degradation of acetone and higher ketones via carboxylation by newly isolated denitrifying bacteria" *J. Genl. Microbiol.*, 135:883-891 (1989).
L. A Robertson, et al. "Thiosphaera pantotropha gen. nov. sp. nov., a facultatively abaerobic, facultatively autotrophic sulphur bacterium" *J. Genl. Microbiol.* 129:2847-2855 (1983).
D. G. Taylor, et al., "The microbial metabolism of acetone" *J. Genl. Microbiol.* 118:159-170 (1980).
J. R. Vestal, et al., "Divergent metabolic pathways for propane and propionate utilization by a soil isolate" *J. Bacteriol.* 99:216-221 (1969).
F. Widdell, "Growth of methanogenic bacteria in pure culture with 2-propanol and other alcohols as hydrogen donors" *Appl. Environ. Microbiol.* 51:1056-1062 (1986).
F. Widdel, et al., "Studies on dissimilatory sulfate-reducing bacteria that decompose fatty acids. I. Isolation of new sulfate-reducing bacteria enriched with acetate from saline environments. Description of *Desulfobacter postgatei* gen. nov., sp. nov." *Arch. Microbiol.* 129:395-400 (1981).
F. Widdel, et al., "Studies on dissimilatory sulfate-reducing bacteria that decompose fatty acids. III. Characterization of the filamentous gliding *Desulfonema limicola* gen. nov., sp. nov., and *Desulfonema magnum* sp nov." *Arch. Microbiol.* 134:286-294 (1983).

*Primary Examiner*—Herbert J. Lilling
*Attorney, Agent, or Firm*—Fulbright & Jaworski

[57] ABSTRACT

The present invention provides an economical and efficient method for the elimination and biodegradation of soil and groundwater containing polar organic solvents, especially acetone. The bioremediation methods of the present invention comprise contacting the bacteria *Xanthomonas maltophilia* or *Bacillus thuringiensis* with the contaminated medium under appropriate conditions. In addition, the present invention provides for a composition of matter useful in the bioremediation of a medium, e.g., groundwater or soil contaminated with polar organic compounds, such as acetone.

23 Claims, No Drawings

BIOREMEDIATION OF POLAR ORGANIC COMPOUNDS

BACKGROUND OF THE INVENTION

1. Field of the Invention

This invention relates generally to the field of bioremediation. More particularly, the present invention relates to the bioremediation of media contaminated with volatile polar organic compounds. Even more particularly, the present invention relates to the bioremediation of media contaminated with acetone.

2. Description of the Related Art

Volatile polar organics, such as acetone, are widely used as industrial solvents and feed stocks for manufacturing processes. The storage and transportation of these substances require tanks and pipelines. Any structural failure of these tanks or pipelines impacts on the physical and economical vitality of the contaminated area. Any resulting contamination damages the ecosystem locally, killing indigenous plants and life.

Presently, there are few adequate methods of decontaminating groundwater containing volatile polar organics. One possible technique, air stripping, involves blowing air through water. The principle of this method is that air is more soluble in water than volatile organics, thus the volatile organics are displaced. This technique works well for non-polar organics, but volatile polar organics, such as acetone, are too soluble in water to be efficiently displaced.

A second method of bioremediating contaminated media involves absorption on activated carbon. This method has been used successfully for non-polar organics, but suffers from a number of disadvantages for use in bioremediating volatile polar organics. The technique is relatively expensive and disposal of the absorbed organics poses its own environmental problems. Ideally, the activated carbon traps are regenerated by removing the trapped organics using a variety of methods including solvent extraction. The organics must then be disposed of, usually by transportation away from the site, thus involving risks and liability associated with accidental spills.

Thus, it can be seen that bioremediation of contaminated media such as groundwater, sludge or soil is not a simple problem. A great need exists for a satisfactory method of bioremediating media contaminated with volatile polar organics, such as acetone.

SUMMARY OF THE INVENTION

An object of the present invention is a rapid, effective method of bioremediating a medium contaminated with volatile polar organic compounds.

An additional object of the present invention is the formation of a novel composition of matter useful in the bioremediation of a medium contaminated with volatile polar organic compounds.

Yet another object of the present invention is to provide an economical and efficient method of decontaminating groundwater containing acetone.

The present invention provides a rapid and effective method of bioremediating groundwater or soil contaminated with a volatile polar organic compounds, such as, acetone. More specifically, the identification of two microorganisms capable of biodegrading acetone is disclosed.

In one embodiment of the present invention, there is provided a composition of matter useful for the bioremediation of groundwater or soil contaminated with volatile polar organic compounds including acetone. The composition of matter is composed of from about 1% to about 99% bacteria capable of degrading polar organic compounds and a diluent.

In another embodiment, the present invention provides a method for bioremediating a liquid or solid medium contaminated with volatile polar organic substances such as acetone. The method comprises contacting a sufficient amount of bacteria for a sufficient length of time under conditions which allow for the bacteria to degrade the organic compounds.

Significant biodegradation is found with *Xanthomonas maltophilia* and *Bacillus thuringiensis*. The present invention will be a useful and efficient means to bioremediate acetone-contaminated groundwater supplies.

Other and further objects, features and advantages will be apparent and eventually more readily understood from a reading of the following specification, where examples of the present preferred embodiments of the invention are given for the purpose of disclosure.

DETAILED DESCRIPTION OF THE INVENTION

As used herein "volatile polar organic" refers to organic compounds with 1 to 5 carbon atoms and 1 to 6 oxygen atoms per molecule. For example, this includes solvents, synthetic intermediates, and compounds of general industrial use, such as alcohols, aldehydes, epoxides, ethers, and ketones.

In one embodiment of the present invention, there is provided a method of bioremediating a liquid or a solid medium contaminated with volatile polar organic compounds. The method comprises the steps of contacting bacteria in the presence of an inorganic nutrient with the medium under conditions which degrade the polar organic substances.

The inorganic nutrients may be any that allow for the bacteria to degrade the organic compound. Preferably, the inorganic nutrients are the mineral salts.

Optionally, an organic co-substrate may be combined with the bacteria and inorganic nutrient. The co-substrate may be any that allows for the bacteria to degrade the organic compounds. Most preferably, the co-substrate is yeast extract.

The bacteria may be in contact with the medium for any length of time necessary to ensure biodegradation of the organic substances. Preferably, the bacteria are in contact with the medium for a length of time of greater than 12 hours.

The bacteria may be in contact with the medium at any temperature which will allow for a biodegradation of the organic substances. Preferably the bacteria would be in contact with the medium at a temperature of from about 10° C. to about 45° C. Most preferably, the contacting temperature is about 15° C. to about 40° C.

The bacteria may be in contact with the medium at any pH that will allow for biodegradation of the organic substances. Preferably the bacteria are in contact with the medium at a pH of from about 6 to about 8. Most preferably, the pH of the medium is about 6.9.

The method for bioremediating a liquid or a solid medium contaminated with organic substances may occur in any facility that allows for the method of the present invention to degrade the organic compounds. Preferably, the contacting steps of the method of the present invention occurs substantially in situ. The novel method of the present invention may be used to bioremediate a wide variety of liquid or solid media contaminated with volatile polar organic compounds. For example, the methods of the present invention may be used to bioremediate groundwater, soil, surface water, sludge and water.

The microorganisms useful in the methods of the present invention may be isolated from the specific site and subsequently reapplied (indigenous, naturally occurring microbes), or they may be obtained from an external source for application to the site (nonindigenous, naturally occurring microbes), generally supplied as frozen, dried, or freeze-dried cultures. One skilled in the art readily recognizes that genetically-altered (recombinant) microorganisms are useful in the methods of the present invention.

The present invention also provides a method of bioremediating a container contaminated with polar organic compounds. This method comprises the step of contacting a sufficient amount of bacteria and an inorganic nutrient to said container under conditions which allow the bacteria to biodegrade organic compounds.

In another embodiment, the present invention provides a method of bioremediating groundwater contaminated with acetone. This method comprises the steps of contacting a sufficient amount of bacteria, mineral salts and a yeast extract to the groundwater for greater than 12 hours. The contacting is carried out at a temperature between 10° C. and 45° C. and at a pH of between 6 and 8. The bacteria used to bioremediate the groundwater contaminated with acetone is selected from the group consisting of *Bacillus thuringiensis* and *Xanthomonas maltophilia*. This method may also be used to bioremediate water contaminated with acetone.

In addition to the methods of the instant invention, there is also provided a novel composition of matter. This composition, useful for bioremediating an organic compound-contaminated medium, e.g., groundwater, is comprised of bacteria capable of degrading polar organic compounds.

The bacterial component of this composition may be any that degrades volatile polar organic compounds. Most preferably, the bacteria are *Bacillus thuringiensis* or *Xanthomonas maltophilia*. The bacterial component may be present in an amount greater than 1% of the composition.

Optionally, the composition of matter of the present invention may contain a diluent. The diluent component may be any that provides a chemical vehicle for the bacterial component. Most preferably, the diluent is water.

EXAMPLE 1

Isolation and Identification of Acetone-Degrading Microorganisms

The isolation and identification of acetone-degrading microorganisms, *Bacillus thuringiensis* and *Xanthomonas maltophilia* was by well established methods of fatty acid chemotaxonomy and other classical microbiological taxonomic methods. E. H. Lennette, A. Balows, N. J. Hausler, Jr. and J. P. Truant, *Manual of Clinical Microbiology*, 3rd Edition, 1980. Briefly, this method consists of isolating the acetone-degrading microorganisms by serially diluting the solution containing acetone and unknown bacteria. After several 1:10 dilutions, a 0.1 mL aliquot was placed on an agar plate to isolate an individual colony or colonies of aerobic microorganisms. The isolated individual colonies of microorganisms were then grown in acetone as carbon base.

The acetone-degrading microorganisms were identified by hydrolyzing the cell membranes and isolating fatty acids from these membranes. The fatty acids were converted into their methyl esters to enhance stability. These esters were injected into a gas chromatograph to determine their relative concentrations. The profile of these relative concentrations was compared with known fatty acid profiles of bacteria and a match obtained.

EXAMPLE 2

Gas Chromatographic Analysis for Evaluation of Acetone Biodegradation Using the Direct Aqueous Injection Method The analytical instrument used was a Hewlett Packard 5890 Gas Chromatograph. A 50 m '0.32 mm 2.0 $\mu$m methylsilicone column was used isothermally at 106° C. and 1-$\mu$L aliquots of each test bottle sample were taken at time intervals of 0, 24, and 48 hours after thorough mixing and injected into the gas chromatograph, where the injection port temperature was set at 104° C. The retention times of 100 ppm acetone in Basal Salts Media (both in $dH_2O$ and $gH_2O$ base) is estimated to be at 2.8 to 2.9 mins.

EXAMPLE 3

Preparation of Test Sample for Determining the Rate of Acetone Degradation with Microorganisms To prepare the microorganism inoculums, acetone-degrading isolates were preincubated in a 250-mL Erlenmeyer flask that contained 125 mL of autoclaved Basal Salts Media [(2.5 g ammonium chloride, 0.9 g dibasic potassium phosphate, 1.2 g dibasic sodium phosphate (mineral salts)] and 0.5% yeast extract dissolved in 1 L distilled water ($dH_2O$) base, pH adjusted to 6.9) plus 1% glucose as carbon source for the initial incubation phase. The individual microorganisms plus Basal Salts Media were incubated for 24 hours at room temperature in a Lab-Line Orbit Environ-Shaker set at 150 rpm shaking speed. Then the microorganisms were transferred in 25 mL aliquots of the initial incubation phase inoculum preparation into another 250-mL Erlenmeyer flask with 100 mL Basal Salts Media having 4% acetone sterile filtered into Basal Salts Media as the carbon source instead of glucose. This second phase incubation mixture was incubated under similar incubation conditions for another 24 hours.

Once the microorganisms have reached stationary phase we adjusted the inoculum size using MacFarland turbidity standards and a spectrophotometer to obtain a uniformly-sized inoculum of approximately $10^9$ microorganisms/mL. The MacFarland turbidity standards are used for determining densities of bacterial suspensions. A 0.3 mL of 1% barium chloride solution was mixed with 9.7 mL of 1% sulfuric acid. The resulting turbidity corresponds to a cell density of approximately $9 \times 10^8$ per mL.

The test sample was prepared at 100 ppm acetone concentration by dispensing 1 mL of the adjusted inoculum into a 50-mL Wheaton serum bottle together with 10 mL of Basal Salts Media containing 100 ppm acetone. The bottles were then sealed with Teflon-lined rubber stoppers and crimp caps. Two different sets of test bottle samples were so prepared. The test bottle samples differed in the type of water bases prepared as Basal Salts Media. One test set used 1 L of distilled water (dH₂O) and the other used 1 L of 0.2-μm filter-sterilized groundwater (gH₂O) that was obtained from a 600 foot groundwater table source at the University of Houston Coastal Center, La Marque, Tex. The first set of test bottle samples contained 100 ppm acetone in Basal Salts Media (gH₂O base) with their respective microorganisms, i.e., either *Bacillus thuringiensis or Xanthomonas maltophilia*. The second set of test bottle samples contained 100 ppm acetone in Basal Salts Media (dH₂O base) including their respective microorganisms. The controls were 100 ppm acetone in either Basal Salts Media with gH₂O or dH₂O base minus the microorganisms, i.e., either *Bacillus thuringiensis* or *Xanthomonas maltophilia*. The test bottle samples were incubated for periods of 24 and 48 hours under the same incubation conditions, i.e., for 24 hours at room temperature.

EXAMPLE 4

Biodegradation of Acetone with *Bacillus thuringiensis* and *Xanthomonas maltophilia* after 24 hours and 48 hours of Incubation

TABLE I

Biodegradation of 100 ppm of acetone after 24 hours of incubation

| BS Medium | Inoculum | Acetone Concentration (ppm) Initial | Final | % Remaining |
|---|---|---|---|---|
| Distilled Water | None | 100 | 114 | 114 |
| Groundwater | None | 100 | 112 | 112 |
| Distilled Water | Bacillus thuringiensis | 100 | 83 | 83 |
| Groundwater | Bacillus thuringiensis | 100 | 8 | 8 |
| Distilled Water | Xanthomonas maltophilia | 100 | 77 | 77 |
| Groundwater | Xanthomonas maltophilia | 100 | 67 | 67 |

Tables I and II depict the biodegradation of 100 ppm acetone with *Bacillus thuringiensis* and *Xanthomonas maltophilia* after 24 and 48 hours, respectively, of incubation. A 24 hour incubation of groundwater containing acetone with *Bacillus thuringiensis* bacteria resulted in almost complete degradation of the acetone. The bacteria *Xanthomonas maltophilia*, while less effective in degrading acetone than *Bacillus thuringiensis*, also significantly degraded acetone in groundwater.

In conclusion, therefore, it seen that the present invention and the embodiments disclosed herein are well adapted to carry out the objectives and obtain the ends set forth at the outset. Certain changes can be made in the method without parting from the spirit and scope of this invention.

TABLE II

Biodegradation of 100 ppm of acetone after 48 hours of incubation

| BS Medium | Inoculum | Acetone Concentration (ppm) Initial | Final | % Remaining |
|---|---|---|---|---|
| Distilled Water | None | 100 | 97 | 97 |
| Groundwater | None | 100 | 119 | 119 |
| Distilled Water | Bacillus thuringiensis | 100 | 80 | 80 |
| Groundwater | Bacillus thuringiensis | 100 | 6 | 6 |
| Distilled Water | Xanthomonas maltophilia | 100 | 76 | 76 |
| Groundwater | Xanthomonas maltophilia | 100 | 76 | 76 |

One skilled in the art will readily appreciate that the present invention is well adapted to carry out the objects and obtain the ends and advantages mentioned, as well as those inherent therein. The compounds, methods, procedures and techniques described herein are presently representative of the preferred embodiments, are intended to be exemplary and not intended as limitations of the scope. Changes therein and other uses will occur to those skilled in the art which are encompassed within the spirit of the invention or defined by the scope of the appended claims.

All publications mentioned in this specification are indicative of the level of skill of those skilled in the art to which the invention pertains. All publications are herein incorporated by reference to the same extent as if the individual publication has specifically and individually indicated to be incorporated by reference.

What is claimed is:

1. A method for the bioremediation of a medium contaminated with ketones, comprising the steps of:
    contacting a sufficient amount of an isolated and identified ketone degrading bacteria of the species *Bacillus thuringiensis* and an organic nutrient to said medium under conditions which allow said bacteria to biodegrade said ketone.

2. The method of claim 1, further comprising adding a co-substrate.

3. A method according to claim 2, wherein said co-substrate is yeast extract.

4. A method according to claim 1, wherein said bacteria are selected from the group consisting of the genus *Xanthomonas*.

5. A method of claim 1, wherein said conditions include a length of time greater than about 12 hours.

6. A method of claim 1, wherein said conditions include contacting that occurs at a temperature of from about 10° C. to about 45° C.

7. A method of claim 1, wherein said conditions include contacting that occurs at a pH of from about 6 to about 8.

8. The method of claim 1, wherein said conditions include a pH that is 6.9.

9. A method of claim 1, wherein said medium is groundwater.

10. The method of claim 1, wherein the medium is soil.

11. The method of claim 1, wherein the medium is surface water.

12. The method of claim 1, wherein the medium is sludge.

13. The method of claim 1, wherein the medium is water.

14. The method according to claim 1, wherein said inorganic nutrients are mineral salts.

15. The method of claim 1, wherein said bacteria are genetically altered.

16. A method of bioremediating a container contaminated with ketones, comprising the steps of:

contacting a sufficient amount of bacteria of an isolated and identified ketone degrading bacteria of the species *Bacillus thuringiensis* and an inorganic nutrient to said container under conditions which allow said bacteria to biodegrade said ketones.

17. A method of bioremediating groundwater contaminated with a ketone, comprising the steps of contacting a sufficient amount of bacteria, mineral salts, and a yeast extract for greater than 12 hours, at a temperature between 10° C. and 45° C., and at a pH of between 6 and 8, wherein said bacteria are of the species *Bacillus thuringiensis.*

18. The method of claim 17, wherein said ketone is acetone.

19. A method of bioremediating water contaminated with ketone, comprising the steps of:

contacting a sufficient amount of bacteria, mineral salts, and a yeast extract for greater than 12 hours, at a temperature of 10° C. to 45° C. and a pH of between 6 and 8, wherein said bacteria are of the species *Bacillus thuringiensis*.

20. The method of claim 19, wherein said ketone is acetone.

21. The method of claim 17, wherein said pH is 6.9.

22. The method of claim 18, wherein said pH is 6.9.

23. The method of claim 1, wherein the contacting of the medium occurs in situ.

* * * * *